US010195182B2

(12) United States Patent
Song

(10) Patent No.: US 10,195,182 B2
(45) Date of Patent: *Feb. 5, 2019

(54) ITE FOR CANCER INTERVENTION AND ERADICATION

(71) Applicant: Ariagen, Inc., Menlo Park, CA (US)

(72) Inventor: Jiasheng Song, Madison, WI (US)

(73) Assignee: Ariagen, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/613,808

(22) Filed: Jun. 5, 2017

(65) Prior Publication Data

US 2017/0333401 A1 Nov. 23, 2017

Related U.S. Application Data

(60) Continuation of application No. 14/961,325, filed on Dec. 7, 2015, now Pat. No. 9,694,000, which is a continuation of application No. 13/952,030, filed on Jul. 26, 2013, now Pat. No. 9,238,645, which is a division of application No. 13/503,657, filed as application No. PCT/US2010/052729 on Oct. 14, 2010, now Pat. No. 8,604,067.

(60) Provisional application No. 61/257,422, filed on Nov. 2, 2009.

(51) Int. Cl.

| A61K 31/427 | (2006.01) |
| *A61P 35/00* | (2006.01) |
| *A61K 31/40* | (2006.01) |
| *A61K 31/425* | (2006.01) |
| *A61K 31/475* | (2006.01) |
| *A61K 45/06* | (2006.01) |
| *C07D 417/06* | (2006.01) |

(52) U.S. Cl.
CPC ............ *A61K 31/427* (2013.01); *A61K 31/40* (2013.01); *A61K 31/425* (2013.01); *A61K 31/475* (2013.01); *A61K 45/06* (2013.01); *C07D 417/06* (2013.01)

(58) Field of Classification Search
USPC ....................................................... 514/365
See application file for complete search history.

(56) References Cited

U.S. PATENT DOCUMENTS

| 6,916,834 | B2 | 7/2005 | DeLuca et al. |
| 7,002,019 | B2 | 2/2006 | DeLuca et al. |
| 7,419,992 | B2 | 9/2008 | DeLuca et al. |
| 2002/0177594 | A1 | 11/2002 | Curtin et al. |
| 2012/0214853 | A1 | 8/2012 | Song |
| 2013/0338201 | A1 | 12/2013 | Song |

FOREIGN PATENT DOCUMENTS

| EP | 1842541 A1 | 10/2007 |
| WO | 98/39330 | 9/1998 |
| WO | 0228832 | 4/2002 |
| WO | 02064138 | 8/2002 |
| WO | 03/068742 | 8/2003 |
| WO | 2004/060888 | 7/2004 |
| WO | 2006029862 | 3/2006 |
| WO | 2009/070645 | 4/2009 |
| WO | 2009/067349 A2 | 5/2009 |
| WO | 2013/033003 | 3/2013 |
| WO | 2013/041468 | 3/2013 |

OTHER PUBLICATIONS

USPTO, PTAB decision on the appeal of U.S. Appl. No. 13/954,834, 17 pages (May 30, 2018).
Akahoshi et al., "Synthesis, structure-activity relationships, and pharmacokinetic profiles of nonpeptidic α-Keto hHeterocycles as novel inhibitors of human chymase," J. Med. Chem. 44:1286-1296 (2001).
Bermúdez et al., "Beta-naphthoflavone represses dystrophin Dp71 expression in hepatic cells," Biochim. Biophys. Acta. 1759(3-4):152-158 (2006).
Bock et al., "Ah receptor- and TCDD-mediated liver tumor promotion: clonal selection and expansion of cells evading growth arrest and apoptosis," Biochem. Pharmacol. 69(10):1403-1408 (2005).
Brauze et al., "The effect of aryl hydrocarbon receptor ligands on the expression of AhR, AhRR, ARNT, Hif1alpha, CYP1A1 and NQO1 genes in rat liver," Toxicol. Lett. 167(3):212-220 (2006).
"Fruit juice and medications don't mix," Consumer Reports News (Sep. 2, 2008).
Cook et al., "Angiogenesis Inhibitors: Current Strategies and Future Prospects," http://cajournal.org (2010).
Dietrich et al., "The aryl hydrocarbon receptor (AhR) in the regulation of cell-cell contact and tumor growth," Carcinogenesis 31(8):1319-1328 (2010).
Ebos et al., "Accelerated metastasis after short-term treatment with a potent inhibitor of tumor angiogenesis," Cancer Cell 15(3):232-239 (2009).
Elizondo et al., "Altered cell cycle control at the G(2)/M phases in aryl hydrocarbon receptor-null embryo fibroblast," Mol Pharmacol 57(5):1056-63 (2000).
Ellis, "Role of Angiogenesis Inhibitors in Cancer Treatment," Oncology 15:39-46 (2001).

(Continued)

*Primary Examiner* — Kathrien A Cruz
(74) *Attorney, Agent, or Firm* — Steptoe & Johnson LLP; Z. Ying Li; Dong I. Chen

(57) ABSTRACT

A method of cancer intervention or eradication by administering an effective amount of an endogenous ligand for the aryl hydrocarbon (Ah) receptor (AhR) named ITE or one of its analogs (the active ingredient) to a subject with cancer is disclosed. An effective dose and dosing frequency of the active ingredient are determined by measuring its blood levels of the subject after dosing. The active ingredient formulated with a carrier system is applied topically, enterally, or parenterally to the subject. The formulated drug can also be administered together with one or more of other cancer therapeutic agents. A maintenance dosing is provided after the subject is free of cancer to insure the cancer eradication. Subjects with cancers of prostate, liver, lung, ovarian, and breast are preferably accepted for treatment.

10 Claims, 3 Drawing Sheets

(56) References Cited

OTHER PUBLICATIONS

English et al., "VEGF inhibition and metastasis: possible implications for anti angiogenic therapy," Cancer Biol. Ther. 3(13):1214-1225 (2009).
Fritz et al., "The selective aryl hydrocarbon receptor modulator 6-methyl-1,3,8-trichlorodibenzofuran inhibits prostate humor metastasis in TRAMP mice," Biochem. Pharmacol. 77(7):1151-1160 (2009).
Fuganti et al., "A general method for the synthesis of the most powerful naturally occurring Maillard flavors," Tetrahedron 63:4762-4767 (2007).
Gierthy et al., "Correlation of in vitro and in vivo growth suppression of MCF-7 human breast cancer by 2,3,7,8-tetrachlorodibenzo-p-dioxin," Cancer Res 53(13):3149-3153 (1993).
Gluschnaider et al., "beta-TrCP inhibition reduces prostate cancer cell growth via upregulation of the aryl hydrocarbon receptor," PLoS ONE 5(2):e9060 (2010).
Hall et al., "Activation of the Aryl-Hydrocarbon Receptor Inhibits Invasive and Metastatic Features of Human Breast Cancer Cells and Promotes Breast Cancer Cell Differentiation," Mol Endocrinol 24:359-369 (2010).
Henry et al., "A potential endogenous ligand for the aryl hydrocarbon receptor has potent agonist activity in vitro and in vivo," Arch. Biochem. Biophys. 450(1):67-77 (2006).
Heravi et al., "An efficient synthesis ofthiazol-2-imine derivatives via a onepot, three-component reaction," Tetrahedron Letters 53:392-394 (2012).
Holcomb et al., "Inhibition of 7,12-dimethylbenzanthracene-induced rat mammary tumor growth by 2,3,7,8-tetrachlorodibenzo-p-dioxin," Cancer Lett 82(1):43-7 (1994).
Ishida et al., "Activation of the aryl hydrocarbon receptor pathway enhances cancer cell invasion by upregulating the MMP expression and is associated with poor prognosis in upper urinary tract urothelial cancer," Carcinogenesis 31 (2):287-295 (2010).
Jana et al., "Cross-talk between 2,3,7,8-tetrachlorodibenzo-p-dioxin and testosterone signal transduction pathways in LNCaP prostate cancer cells," Biochem Biophys Res Commun 256(3):462-8 (1999).
John et al., "Antiangiogenic therapy and surgical practice," Br J Surg 95(3):281-293 (2008).
Johnson, et al., "Total synthesis of (-)-Rhazinilam: asymmetric C—H bond activation via the use of chiral auxiliary," J. Am. Chem. Soc. 124:6900-6903 (2002).
Jux et al., "Langerhans cell maturation and contact hypersensitivity are impaired in aryl hydrocarbon receptor-null mice," J. Immunol. 182(11):6709-6717 (2009).
Kajta et al., "Aryl hydrocarbon receptor-mediated apoptosis of neuronal cells: a possible interaction with estrogen receptor signaling," Neuroscience 158(2):811-822 (2009).
Kawajir, et al., "Aryl hydrocarbon receptor suppresses intestinal carcinogenesis in ApcMin/+ mice with natural ligands," Proc. Nati. Acad. Sci. U.S.A. 106(32):13481-13486 (2009).
Kerbel, "Tumor angiogenesis: past, present and the near future," Carcinogenesis 21:505-515 (2000).
Knerr et al., "Carcinogenicity of 2,3,7,8-tetrachlorodibenzo-p-dioxin in experimental models," Mol Nutr Food Res, 50(10):897-907 (2006).
Koliopanos et al., "Increased arylhydrocarbon receptor expression offers a potential therapeutic target for pancreatic cancer," Oncogene 21(39):6059-70 (2002).
Loges et al., "Silencing or fueling metastasis with VEGF inhibitors: antiangiogenesis revisited," Cancer Cell 15(3):167-170 (2009).
Lo Piparo et al., "Virtual screening for aryl hydrocarbon receptor binding prediction," J Med Chem. 49(19):5702-5709 (2006).
Marlowe et al., "The aryl hydrocarbon receptor displaces p300 from E2F-dependent promoters and represses S phase-specific gene expression," J Biol Chem 279(28):29013-22 (2004).
McDougal et al., "Inhibition of 7,12-dimethylbenz[a] anthracene-induced rat mammary tumor growth by aryl hydrocarbon receptor agonists," Cancer Lett.120(1):53-63 (1997).
McDougal et al., "Tamoxifen-induced antitumorigenic/antiestrogenic action synergized by a selective aryl hydrocarbon receptor modulator," Cancer Res. 61(10):3902-3907 (2001).
Milinkevich et al., "Synthesis of 5-(Thiazol-5-yl)-4,5-dihydroisoxazoles from 3-Chloropentane-2,4-dione," J. Comb. Chem. 10:521-525 (2008).
Mizzoni et al., "Some thiazolines and thiazolidinones with antituberculous activity," (Jul. 5, 1958).
Mjambili et al., "Synthesis and biological evaluation of 2-aminothiazole derivatives as antimycobacterial and antiplasmodial agents," Biorganic & Medicinal Chemistry Letters 24:560-564 (2014).
Morrow et al., "Aryl hydrocarbon receptor-mediated inhibition of LNCaP prostate cancer cell growth and hormone-Induced transactivation," J. Steroid Biochem. Mol. Biol. 88(1):27-36 (2004).
Narender et al., "Aqueous phase synthesis of thiazoles and aminothiazoles in the presence of β-cyclodextrin," Tetrahedron letters 46:5953-5955 (2005).
O'Donnell et al., "The aryl hydrocarbon receptor mediates leflunomideinduced growth inhibition of melanoma cells," PLoS One 7:e40926 (2012).
Oenga et al., "TCDD and PCBs inhibit breast cancer cell proliferation in vitro," Toxicol In Vitro. 18(6):811-9 (2004).
Okino et al., "Toxic and chemopreventive ligands preferentially activate distinct aryl hydrocarbon receptor pathways: Implications for cancer prevention," Cancer Prev Res (Phila Pa). 2(3):251-256 (2009).
Ozawa et al., "A new synthesis of glutathione via the thiazoline peptide," Bull. Chem. Soc. Jpn., 53:2592-2593 (1980).
Paez-Ribes et al., "Antiangiogenic therapy elicits malignant progression of tumors to increased local invasion and distant metastasis," Cancer Cell 15(3):220-231 (2009).
Park et al., "The aryl hydrocarbon receptor predisposes hepatocytes to Fasmediated apoptosis," Mol Pharmacol. 67(3):612-22 (2005).
Patani et al., "Bioisosterism: A Rational Approach to Design," Chemical Reviews 96:3147-3176 (1996).
Peng et al., "Potential therapeutic significance of increased expression of aryl hydrocarbon receptor in human gastric cancer," World J. Gastroenterol. 15(14):1719-1729 (2009).
Poland et al., "2,3,7,8-tetrachlorodibenzo-p-dioxin and related halogenated aromatic hydrocarbons: examination of the mechanism of toxicity," Annu. Rev. Pharmacol. Toxicol. 22:517-554 (1982).
Puga et al., "Ah receptor signals cross-talk with multiple developmental pathways," Biochem Pharmacol. 69(2):199-207 (2005).
Puga et al., "Role of the aryl hydrocarbon receptor in cell cycle regulation," Toxicology 181-182:171-7 (2002).
Quintana et al., "Control of T(reg) and T(H)17 cell differentiation by the aryl hydrocarbon receptor," Nature 453(7191):65-71 (2008).
Ray et al., "Activation of the aryl hydrocarbon receptor by TCDD inhibits senescence: a tumor promoting event?" Biochem. Pharmacol. 77(4):681-688 (2009).
Rose, "A theory of the action of cancer chemotherapeutic drugs," Clin. Exp. Immunol. 2:361-373 (1967).
Roukos et al., "Current concerns and challenges regarding tailored antiangiogenic therapy in cancer," Expert Rev Anticancer Ther. 9(10):1413-1416 (2009).
Safe et al., "Mechanism of action and development of selective aryl hydrocarbon receptor modulators for treatment of hormone-dependent cancers," Int J Oncol. 20(6):1123-8 (2002).
Sanderson et al., "2,3,7,8-Tetrachlorodibenzo-p-dioxin and diindolylmethanes differentially induce cytochrome P450 1A1, 1B1, and 19 in H295R human adrenocortical carcinoma cells," Toxicol. Sci. 61(1):40-48 (2001).
Shin et al., "Bevacizumab: an angiogenesis inhibitor for the treatment of solid malignancies," Clin Ther (11): 1779-802 (2006).
Simon et al., "Estimates of cancer potency of 2,3,7,8-tetrachlorodibenzo(p)dioxin using linear and nonlinear dose-response modeling and toxicokinetics," Toxicol. Sci. 112(2):490-506 (2009).
Singh et al. "Primary peripheral T cells become susceptible to 2,3,7,8-tetrachlorodibenzo-p-dioxin-mediated apoptosis in vitro upon activation and in the presence of dendritic cells," Mol. Pharmacol. 73(6)1722-1735 (2008).

(56) References Cited

OTHER PUBLICATIONS

Solankee, et al., "Thiazoline: synthesis and antitubercular activity of 2-Alkyl/Aryl/-5-(w-carboxy pentyl) thiazolin-4-one," Part II, J. Inst. Chemists (India) vol. 66 (1994).

Song et al., "A ligand for the aryl hydrocarbon receptor isolated from lung," Proc Natl Acad Sci USA. 99(23):14694-9 (2002).

Stevens et al., "The aryl hydrocarbon receptor: a perspective on potential roles in the immune system," Immunology 127(3):299-311 (2009).

Sutter et al., "EGF receptor signaling blocks aryl hydrocarbon receptormediated transcription and cell differentiation in human epidermal keratinocytes," Proc. Nati. Acad. Sci. U.S.A. 106(11):4266-4271 (2009).

Yu et al., "In utero exposure of mice to Dibenzo [a,l]Pyrene produces lymphoma in the offspring: role of Aryl hydrocarbon receptor," Cancer Res 66:(2) (2006).

Van Zandt et al., "Discovery of 3[(4,5,7-Trifluorobenzothiazol-2-yl)methyl]indole-N-acetic acid (lidorestat) and congeners as highly potent and selective inhibitors of aldose reductase for treatment of chronic diabetic complications," J. Med. Chem. 48:3141-3152 (2005).

Veldhoen et al., "The aryl hydrocarbon receptor links TH17-cell-mediated autoimmunity to environmental toxins," Nature 453(7191):106-109 (2008).

Wang, et al., "An endogenous aryl hydrocarbon receptor ligand inhibits proliferation and migration of human ovarian cancer cells," Cancer Letters 340:64-71 (2013).

Zhang, et al., "The aryl hydrocarbon receptor as a target for estrogen receptornegative breast cancer chemotherapy," Endocr. Relat. Cancer, 16(3):835-844 (2009).

Bankoti et al., "Functional and phenotypic effects of AhR activation in inflammatory dendritic cells," Toxicol Appl Pharmacol 246:18-28 (2010).

Henry et al., "TCDD and a Putative Endogenous AhR Ligand, ITE, Elicit the Same Immediate Changes in Gene Expression in Mouse Lung Fibroblasts," Toxicological Sciences 114:90-100 (2010).

Quintana et al., "An endogenous aryl hydrocarbon receptor ligand acts on dendritic cells and T cells to suppress experimental autoimmune encephalomyelitis," Proc Natl Acad Sci U S A 107:20768-73 (2010).

Kashani et al., "Expression of the aryl hydrocarbon receptor (AhR) and the aryl hydrocarbon receptor nuclear translocator (ARNT) in fetal, benign hyperplastic, and malignant prostate," Prostate 37(2):98-108 (1998).

Lin et al., "Overexpression of aryl hydrocarbon receptor in human lung carcinomas," Toxicol Pathol 31(1):22-30 (2003).

Liu et al., "AhR expression is increased in hepatocellular carcinoma," J Mol Histol 44(4):455-61 (2013).

Poellinger, "Mechanistic aspects—the dioxin (aryl hydrocarbon) receptor," Food Addit Contam 17(4):261-6 (2000).

Zhang et al., "Activation of aryl hydrocarbon receptor suppresses invasion of esophageal squamous cell carcinoma cell lines," Tumori 98(1):152-157 (2012).

Classic Bioelectronic isosteres (1 page document and 2 pages of translation).

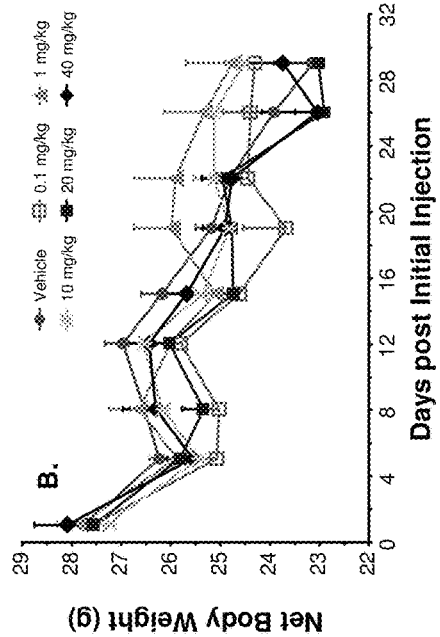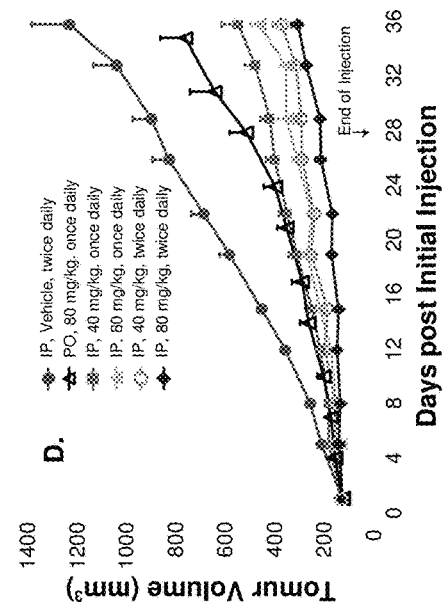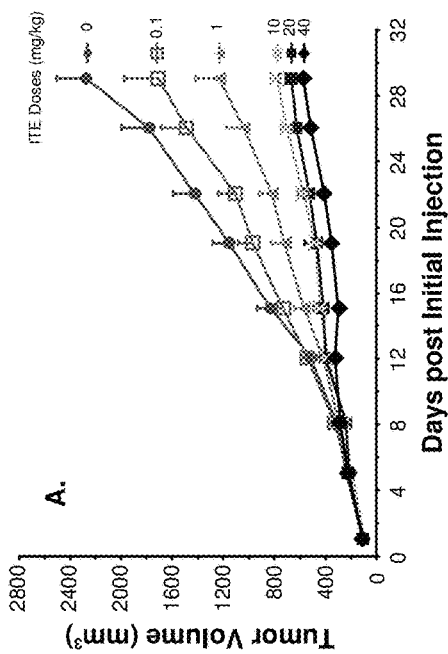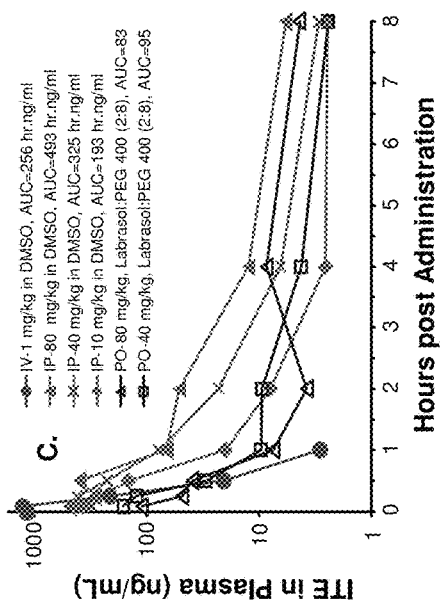
FIG. 1A
FIG. 1B
FIG. 1C
FIG. 1D

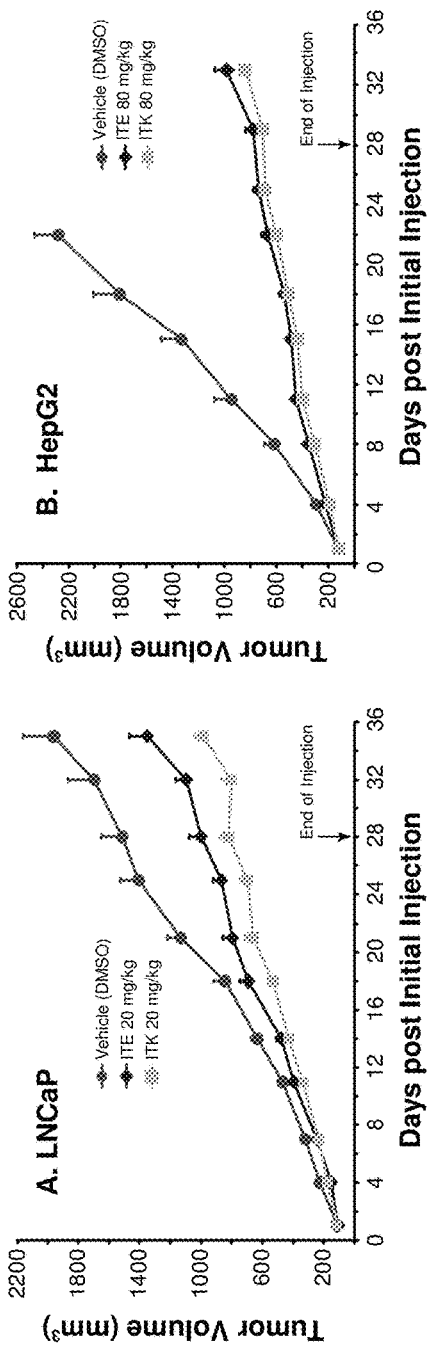
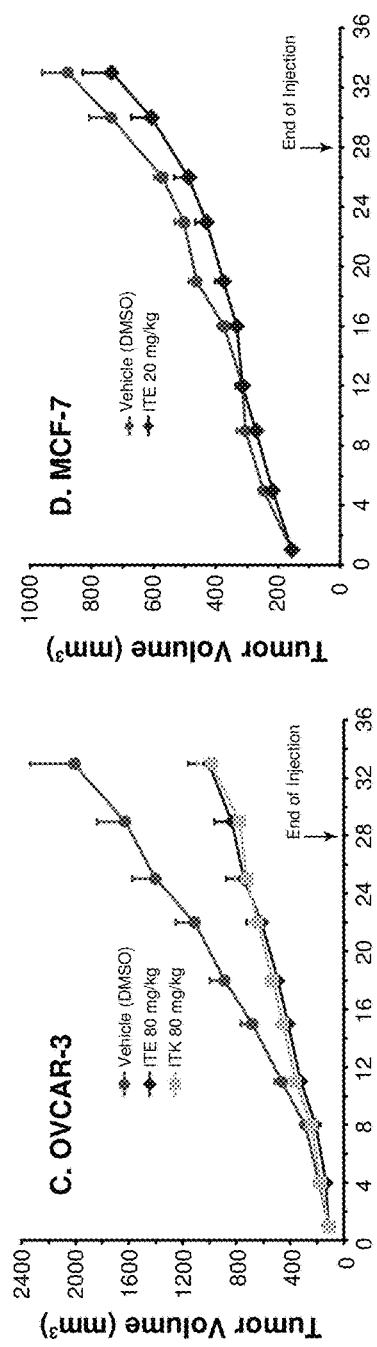

ITE FOR CANCER INTERVENTION AND ERADICATION

TECHNICAL FIELD

Cancer Therapy; Cancer Treatment; Cancer Intervention; Cancer Eradication; Cancer Biology; Oncology; Therapeutics; Pharmaceuticals; Biopharmaceuticals.

BACKGROUND ART

The aryl hydrocarbon (Ah) receptor (AhR) is a ligand inducible transcription factor, a member of a so-called basic helix-loop-helix/Per-Arnt-Sim (bHLH/PAS) superfamily. Upon binding to its ligand, AhR mediates or interacts with a series of biological processes as well as some adverse effects including cell division, apoptosis (programmed cell death), cell differentiation, actions of estrogen and androgen, adipose differentiation, hypothalamus actions, angiogenesis, immune system stimulation or suppression, teratogenicity, tumorigenicity, tumor initiation, tumor promotion, tumor progression, chloracne, wasting syndrome, and actions of other hormonal systems beside the expression of genes of P450 family and others[1,2,3,4,5,6,7,8]. The liganded receptor participates in biological processes through translocation from cytoplasm into nucleus, heterodimerization with another factor named Ah receptor nuclear translocator, attachment of the heterodimer to the regulatory region termed Ah response element of genes under AhR regulation, and then either enhancement or inhibition of transcription of those genes.

The AhR happens to be able to bind, with different affinities, to several groups of exogenous chemicals (thus artificial ligands) such as polycyclic aromatic hydrocarbons exemplified by 3-methylchoranthrene (3-MC) and halogenated aromatic hydrocarbons typified by 2,3,7,8-tetrachlorodibenzo-p-dioxin (TCDD). The receptor system has been studied so far with its artificial ligands. While studies with those AhR artificial ligands helped in advancing our understanding toward the receptor system, thorough elucidation of the physiological roles the system plays and the potential therapeutic benefits the system may offer are impossible without identification of the AhR physiological ligand. As the first step toward this goal, an endogenous ligand for the receptor has been identified. The endogenous ligand, or physiological ligand, or natural hormone, for the AhR was identified as 2-(1'H-indole-3'-carbonyl)-thiazole-4-carboxylic acid methyl ester (ITE)[9,10].

Even though most of the artificial ligands for AhR are environmental toxins[1,2,3] and thus cannot be used as therapeutic agents, for the purpose of understanding functions of liganded AhR, its artificial ligands such as TCDD, 6-methyl-1,3,8-trichlorodibenzofuran (6-MCDF), 8-methyl-1,3,6-trichlorodibenzofuran (8-MCDF), and those derived from indole or tryptophan were used to reveal that the liganded AhR was able to inhibit the metastasis of prostate tumors in a strain of transgenic mice[11] and the growth of carcinogen induced rat mammary tumors[12,13,14], human breast tumor cell xenografts[15,16], and tumors caused by gene mutations[17].

As a natural ligand for AhR, ITE is an excellent agent in targeting precisely and specifically the receptor. The consequence of the targeting, however, is unpredictable from what we have learned so far from the behaviors of those artificial ligands for AhR, with some results showing anitcancer potentials[12,13,14,15,16] while others tumor initiation, promotion, and progression[8,18,19,20,21]. From the fact that it is antiangiogenic, ITE might be useful in cancer therapy[7]. The property of antiangiogenesis alone, however, will not automatically qualify ITE as an effective anticancer agent. There are countless examples proving the point[22,23,24,25]. Many antiangiogenic agents failed to perform as therapeutic agents[22] and lots of others even accelerated tumor invasion and metastasis[26,27] due probably to the stress produced by the agents: limited supply of oxygen and nutrients to the tumors. The antiangiogenic therapy is actually a concern since it may even reduce overall survival, the golden standard for cancer therapy, due to possibly an accelerated metastasis[23]. From the anticancer property of liganded AhR revealed by its artificial ligands[12,13,14,15,16], there is no guarantee that ITE, once bound to the same receptor, may also be able to do even partially what these artificial ligands could do without mentioning the fact that most of those artificial ligands or their metabolites may be highly toxic to those cancer cells being tested. In that sense, those artificial ligands or their metabolites may merely serve as non-discriminative cytotoxic agents, killing cancer cells, not even the results of targeting the Ah receptor.

In addition, a critical factor determines what a liganded receptor will do is the final three dimensional (3D) structure the liganded receptor assumes since it is the 3D structure that dictates how many different cellular factors the liganded receptor will interact with and how these interactions should be carried out to conduct the processes of life. The final 3D structure the liganded receptor assumes is, in turn, solely shaped by the 3D structure of the ligand for the receptor in a given biological system. That is the fundamental basis explaining why the 3D structure of a ligand is so crucial in directing its receptor mediated biological and pharmacological processes. Furthermore, ligands with different structures metabolize differently and their different metabolites will certainly interfere with the biological processes differentially. It is obvious, therefore, that ligands with different 3D structures could then certainly lead to completely different biological consequences even if they can bind to the same receptor.

The validity of the point can be easily established through theoretic reasoning above and of course through illustration of literature data also. For example, even though both TCDD and 6-formylindolo[3,2-b]carbazole (FICZ) are high affinity ligands for AhR, TCDD is found to stimulate Treg cell differentiation, thus suppressing the immune system, while FICZ promote Th17 cell differentiation, thus stimulating the immune system[28]. In another example, both TCDD and ITE are high affinity ligands for AhR but while TCDD induced cleft palate, hydronephrosis, and thymic atrophy, ITE did not do any of these[29]. More examples can be easily found in the literature[30,31,32,33,34]. It is, therefore, not obvious at all that ITE will be a good anticancer agent from those studies with artificial ligands for AhR to show their anticancer property[12,13,14,15,16] or even the study with ITE to prove its antiangiogenic property[7] without an extensive research program with different experimental models and systems to find out a clear answer.

The situation prompted us to investigate whether ITE or one of its structural analogs could be used efficaciously and safely in treating or eradicating cancer. The present invention fully discloses a method of using the newly discovered endogenous Ah receptor ligand ITE or one of its structural analogs as a therapeutic agent in cancer intervention or eradication.

SUMMARY OF INVENTION

Technical Problem

There are two serious problems with current cancer therapies in the market. The first is severe side effects and toxicity. The second is very limited efficacy. Consequently, cancer is still the second leading cause of death in the United States and areas of the world.

The majority of current therapeutic agents for cancer, in both cytotoxic and noncytotoxic categories, are chemicals foreign to the human body. As a result, the body tries extremely hard to get rid of them using whatever metabolic ways available. Since our body does not have a natural and safe way of metabolizing those foreign chemicals, some nonspecific oxidation reactions then are used as major means of metabolism. The consequence is that the elimination processes unavoidably generate a lot of chemically active intermediates or radicals, which will assault also normal cellular substances including, but not limited to, that of immune system's in the body, leading to serious side effects, toxicity, and weakened immune system. Since most of these agents were designed by humans, not nature, they have very high chances to bind to and interact with other cellular factors (including, but not limited to, receptors, enzymes, other proteins) than their expected targets in the body. These "off-target" bindings and interactions account for significant opportunities for side effects.

The effectiveness of cytotoxic agents for cancer therapy is mainly limited by their indiscriminate toxicity to normal cells and tissues including, but not limited to, that of immune system's. The weakened immune system, as expected, makes it impossible to launch an organized assault on cancer cells. The efficacy of noncytotoxic agents, which target specific functions important for the survival of cancer cells, is limited by their single mechanism based strategy. An important hallmark of cancer, however, is their constant genetic changes or mutations. Once a cancer cell changes into a state that it is no longer dependent on a specific function a therapeutic agent targets for survival, the efficacy of the agent will then be lost immediately.

Solution to Problem

The situation thus calls for the emergence of a novel therapeutic agent that can assault cancers with multiple combating capabilities for sustained potency, help immune system at the same time to organize an orchestrated attack on cancers and clean up individual cancer cells for a possible cancer eradication, and limit the chance of "off-target" interaction and metabolize itself safely for low side effect(s). The newly discovered Ah receptor endogenous ligand ITE or one of its structural analogs is capable of satisfying the stringent requirements set forth.

Advantageous Effects of Invention

The most important advantage of the present invention is ITE's or one of its structural analogs' multiple cancer assaulting capabilities to defy the consequence of cancer cells' constant genetic changes. ITE has been demonstrated to inhibit angiogenesis[7]. In literature, the Ah receptor (AhR) liganded with its artificial ligands (not ITE) was shown (possible negative effects of those artificial ligands are ignored here for the moment) to be able to inhibit cell division[35,36,37], promote programmed cell death (apoptosis)[38,39,40], induce cell differentiation[41,42,43], and block actions of estrogen[6,44] and androgen[45,46]. Recently, AhR liganded with artificial ligands (not ITE) has been demonstrated to be able to induce the differentiation of immune T cells[28,47], useful for the immune system in organizing assault on pathogens and cancers. If ITE, or one of its structural analogs, when bound to AhR, can also have one or more of the functions mentioned plus its antiangiogenic property, the multiple cancer assaulting capabilities may make its cancer therapeutic potency sustainable. The sustainability of the potency of ITE or one of its analogs plus its potential ability of stimulating the immune system would not only enhance dramatically the efficacy of the cancer therapy but also make cancer eradication a possibility. The data presented in Drawings and Examples clearly verify the theoretical analysis above.

A huge benefit of using ITE over others in the market is its possibility of low side effect(s) beside its sustainable efficacy backed by its multiple cancer assaulting capabilities. Contrary to those chemicals, including those AhR artificial ligands and the agents used in current cancer therapies, foreign to the human body and designed by humans, ITE is a natural hormone designed by nature and so nature may have designed and implemented a natural and safe way for its metabolism. Its metabolic process thus will cause less or even no problem to the body. This means that it may be low in side effect(s) caused by its metabolism. Another important reason for possible low side effect is that the binding of the natural hormone to its receptor (AhR) is very specific and precise since it is designed by nature, not humans. The natural hormone ITE, other than those human designed chemicals, will then have a low chance of binding to and interacting with other cellular factors to provoke "off-target" problems, important opportunities for side effects. The experimental data described in Drawings and Examples support the point.

Another important issue in cancer therapy is that it is highly desirable for a therapeutic agent specifically working in cancer cells instead of normal cells to enhance its potency and reduce side effects. This type of specificity can be achieved if there are more target molecules the agent binds in cancer cells than in normal cells. The target molecule for ITE and its analogs is AhR. In the literature, the AhR was reported to be highly concentrated in pancreatic cancer tissues from patients but very diluted in all normal pancreatic tissues examined[48]. Similarly, the concentrated AhR is also documented with prostate cancer[49,50] and gastric cancer[51]. This means that the therapeutic specificity of ITE and its structural analogs could be achieved in these reported types of cancers at least.

BRIEF DESCRIPTION OF DRAWINGS

FIGS. 1A-1D show the growth inhibition of human cancer cell line LNCap xenografts in response to doses, routes, and schedules of ITE administration, wherein FIG. 1A shows the degrees of growth inhibition of LNCaP xenografts (mean+SEM, n=8) in response to ITE doses of 0 (vehicle, DMSO), 0.1, 1, 10, 20, and 40 mg/kg b.w. (i.p. injection, every 12 hours for 28 continuous days), and wherein FIG. 1B shows the low toxicity response of the xenograft-bearing mice to the treatment judged by their body weight changes (mean+SEM, n=8), and wherein FIG. 1C shows PK (Pharmacokinetic) profiles of ITE administered (single dosing) i.v., i.p., and p.o. with vehicles used, dosing levels, and AUC's (Area under Curves) as indicated, and wherein FIG. 1D shows the inhibition of LNCaP xenograft growth by ITE at different doses (40 or 80 mg/kg b.w.), schedules (once or twice daily), and routes (i.p. or p.o.) of administration as specified.

FIGS. 2A-2D show shows ITE (diamond) or ITK (one of ITE structural analogs, square) efficacy in inhibiting the growth of xenografts of human prostate (LNCaP), liver (HepG2), ovarian (OVCAR-3), and breast (MCF-7) cancer cell lines (i.p. once daily), wherein FIG. 2A shows inhibition of LNCaP xenograft growth by ITE or ITK at 20 mg/kg for both, and wherein FIG. 2B shows growth inhibition of HepG2 xenografts by ITE or ITK at 80 mg/kg for both, and wherein FIG. 2C shows ITE or ITK inhibiting OVCAR-3 xenograft growth at a dose of 80 mg/kg for both, and wherein FIG. 2D shows a growth inhibition of MCF-7 xenografts by ITE at a dose of 20 mg/kg.

FIGS. 3A-3D show cancer inhibition and eradication by ITE (i.p. once daily) in a syngeneic murine Lewis lung cancer (LLC) model, wherein FIG. 3A shows aggressive growth of LLC tumors and ITE inhibition of tumor growth at a dose of 20 mg/kg, and wherein FIG. 3B shows a better inhibition of LLC tumor growth by ITE at 80 mg/kg (i.p. once daily) so that a treatment program of 28 days plus one more week of post injection observation could be finished, and wherein FIG. 3C shows one mouse (No. 33, diamond) from the ITE group (square) initiating its tumor shrinkage upon the start of the treatment phase, becoming tumor-free at day 13 in the treatment, keeping the tumor-free status during the rest of the treatment phase, and being still tumor-free in an entire one month of the observation phase, and wherein FIG. 3D shows body weight changes of mouse No. 33 (diamond) together with that of ITE (square) and vehicle control (circle) groups.

DESCRIPTION OF EMBODIMENTS

Figure 3B:
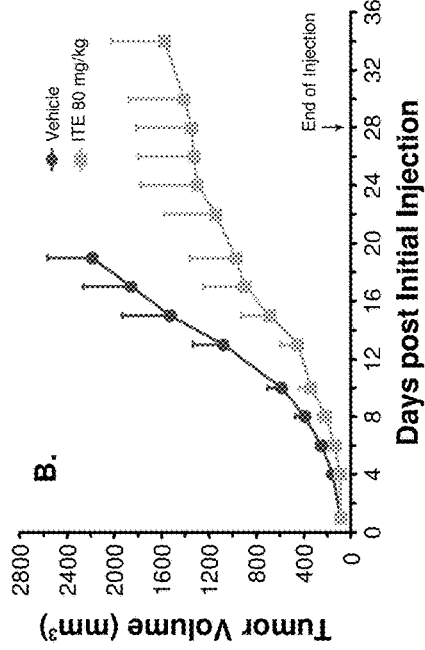

All technical and scientific terms used herein are the same as those commonly used by one of ordinary skill in the art to which the present invention pertains unless defined specifically otherwise. It is understood that other materials and methods similar or equivalent to those described herein can also be used in the practice or in the testing of the present invention but only preferred materials and methods are described below.

The present invention is a method of cancer intervention or eradication with an endogenous aryl hydrocarbon (Ah) receptor (AhR) ligand ITE or one of its structural analogs. ITE or one of its analogs (the active ingredient) can be formulated with one or more pharmaceutically acceptable carrier(s) (the carrier system). The carrier system is consisted of inert materials useful for administering the active ingredient, preferably sterile and nontoxic. The carrier system should be compatible with the active ingredient and can be in a form of solid, liquid, or gas. The properly formulated active ingredient can then be administered topically, enterally, or parenterally to a subject with cancer. It can be provided, for example, in a form of cream, capsules, tablets, lozenges, or injectables. Other compatible ingredients such as preservatives, if needed, could be co-formulated with the active ingredient.

In a preferred intervention program, subjects with cancers of prostate, liver, lung, ovarian, and breast are preferably accepted for treatment with ITE or one of its structural analogs. This is by no mean to limit the therapeutic scope, however. Given the multiple cancer assaulting capabilities that ITE and one of its analogs possesses plus the possibility of stimulation of a subject's immune system to attack cancers and clean up individual cancer cells for possible cancer eradication, the therapeutic scope is envisioned to be expanded quickly in future trials.

In the preferred intervention program, the effective dose range of ITE or one of its structural analogs is determined by measuring the subject's blood concentration of ITE or one of its structural analogs under a specified dosing regimen to establish a concentration-time profile, consulting with an established correlation between the similar concentration-time profiles and effects on cancer inhibition or eradication, which built during a trail or trials as that illustrated in Examples, and balancing the therapeutic effects achievable with the possible toxicity to the subject and health condition or physical durability of the subject. The dosing frequency of ITE or one of its structural analogs is decided similarly as described for the determination of a dose range above. Currently, once a day administration either enterally or parenterally is proposed as preferable with ITE. The dosing will be continued until the subject is free from the cancer. It is preferable to provide a maintenance dosing, whose duration is directed by a trial or trials, after the subject is free of cancer to insure its complete elimination or eradication.

In another preferred intervention program, ITE or one of its structural analogs may be administered in combination with one or more of other cancer therapeutic agents, preferably aiming different therapeutic targets other than AhR. ITE or one of its structural analogs can be formulated either independently from or together with one or more of the other said agents. ITE or one of its structural analogs can be administered either at the same schedule with or different from that of one or more of the other said agents. The proportioning of ITE or one of its structural analogs to one or more of the other cancer therapeutic agents will be directed by a well-designed trial or trials. Combining the therapy of ITE or one of its analogs with one or more of the other cancer therapeutic agents, may further enhance the efficacy. There are lots of examples to show the benefits of combination therapy.

In those preferred intervention programs, the active ingredient is the aryl hydrocarbon (Ah) receptor (AhR) endogenous ligand ITE with the following structural formula (Structural Formula 1):

Structural Formula 1

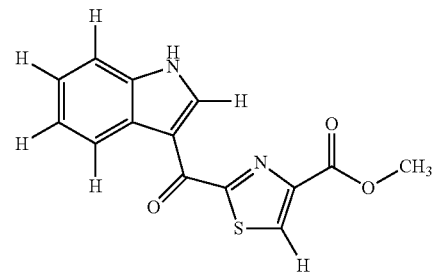

In those preferred intervention programs, the active ingredient can be selected from two especially useful structural analogs of ITE. The said two analogs are envisioned to increase their stability and then extend their half-life in the subjects' systems since either a ketone or thiol ester functional group replaces the normal (oxygen) ester, targeted easily by numerous esterases in biological systems, in the structure of ITE. The extended half-life may translate into higher efficacy and/or longer duration of potency in cancer intervention. The ketone analog (thus termed ITK) of ITE is of the following structural formula (Structural Formula 2):

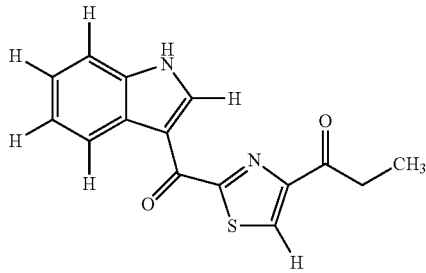

Structural Formula 2

Whereas the structural formula of the thiol (S, sulfur) ester analog (thus termed ITSE) of ITE is as follows (Structural Formula 3):

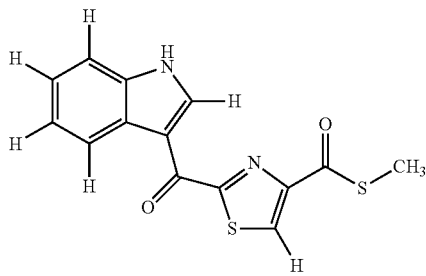

Structural Formula 3

In those preferred intervention programs, the active ingredient can be further selected from the other structural analogs of ITE, specified by the following structural formula (Structural Formula 4):

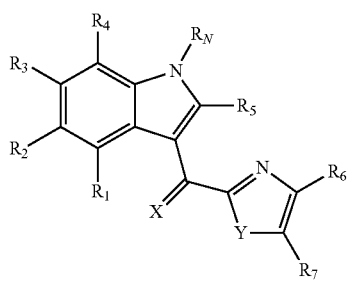

Structural Formula 4 wherein:

X and Y, independently, can be either O (oxygen) or S (sulfur);

$R_N$ can be selected from hydrogen, halo, cyano, formyl, alkyl, haloalkyl, alkenyl, alkynyl, alkanoyl, haloalkanoyl, or a nitrogen protective group;

$R_1$, $R_2$, $R_3$, $R_4$, and $R_5$ can be independently selected from hydrogen, halo, hydroxy (—OH), thiol (—SH), cyano (—CN), formyl (—CHO), alkyl, haloalkyl, alkenyl, alkynyl, amino, nitro (—NO$_2$), alkoxy, haloalkoxy, thioalkoxy, alkanoyl, haloalkanoyl, or carbonyloxy;

$R_6$ and $R_7$, can be independently selected from hydrogen, halo, hydroxy, thiol, cyano, formyl, alkyl, haloalkyl, alkenyl, alkynyl, amino, nitro, alkoxy, haloalkoxy, or thioalkoxy; or $R_6$ and $R_7$, independently, can be:

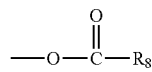

wherein $R_8$ can be selected from hydrogen, halo, cyano, alkyl, haloalkyl, alkenyl, or alkynyl; or $R_6$ and $R_7$, independently, can be:

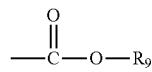

wherein $R_9$ can be selected from hydrogen, halo, alkyl, haloalkyl, alkenyl, or alkynyl; or $R_6$ and $R_7$, independently, can be:

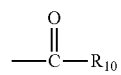

wherein $R_{10}$ can be selected from hydrogen, halo, hydroxy, thiol, cyano, alkyl, haloalkyl, alkenyl, alkynyl, amino, nitro; or $R_6$ and $R_7$, independently, can also be:

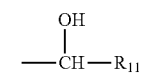

wherein $R_{11}$ can be selected from hydrogen, halo, alkyl, haloalkyl, alkenyl, or alkynyl.

EXAMPLES

Examples from preclinical animal studies will further help the embodiment of the present invention. Use of ITE in inhibition of human prostate cancer growth (Example 1), use of ITE or ITK (one of ITE analogs) in inhibiting the growth of more human cancer types (Example 2), use of ITE in possible cancer eradication (Example 3), and ITE toxicity monitoring (Example 4) will be demonstrated.

Example 1

Materials

Male BALB/c nude mice (*Mus musculus*), 6 to 8 weeks of age, were individually marked by ear coding. The animals were kept in laminar flow rooms at a constant temperature of 20 to 26° C. and humidity of 40 to 70% with 1 animal in each polycarbonate cage (300 mm×180 mm×150 mm). The bedding material was corn cob, which was changed twice weekly. Animals had free access to sterile dry granule food and sterile drinking water during the entire study.

ITE was synthesized by KNC Laboratories Co., Ltd. (Tokyo, Japan). The lot number of the compound is 086-009-2-1 (as lot No.: AHR-001 for AhR Pharmaceuticals). The DMSO (Cat. No.: 0231-500 ML) was manufactured by AMRESCO (Solon, Ohio, USA). The Labrasol was purchased from Gattefosse (Saint-Priest, France) and the PEG 400 was supplied by Sigma (St. Louise, Mo., USA).

Methods

Efficacy Studies

All the procedures related to animal handling, care, and the treatment in the study were performed following guidelines approved by an Institutional Animal Care and Use Committee (IACUC) of Crown Bioscience, Inc. (Santa Clara, Calif., USA, a contract research organization we hired) based on the guidance of the Association for Assessment and Accreditation of Laboratory Animal Care (AAALAC). Animals were checked for any effects of tumor growth and drug treatment on normal behavior such as mobility, food and water consumption, body weight gain/loss (gross body weights were measured twice weekly), eye/hair matting, and any other abnormal effect. Death and observed clinical signs were recorded on the basis of the number of animals within each group. Individual animals with a tumor volume exceeding 3000 mm$^3$ or animals of a group with a mean tumor volume exceeding 2,000 mm$^3$ were euthanized. In addition, animals showing signs of severe distress and/or pain, dropping body weight more than 20% from that at the start of treatment, or losing the capability of accessing adequate food or water were humanely sacrificed.

The human prostate cancer cell line LNCaP (ATCC, American Type Culture Collection, Manassas, Va., USA) were maintained in vitro as monolayer culture in RPMI-1640 medium supplemented with 10% fetal bovine serum (FBS), 100 U/ml penicillin, 100 µg/ml streptomycin, and 2 mM L-glutamine at 37° C. in an atmosphere of 5% $CO_2$ in air. The tumor cells were routinely subcultured twice a week. The cells growing in an exponential phase were harvested and counted for tumor inoculation.

Each mouse was inoculated subcutaneously at the right flank with the LNCaP cells ($1 \times 10^7$) in 0.1 ml of PBS for tumor development. When a mean tumor volume reached around 150 mm$^3$, the tumor-bearing mice were divided into homogeneous blocks based on their tumor volumes followed by a randomization of mice in each block into treatment groups (thus minimizing variations in tumor response to treatments due to the differential in initial mean tumor volumes). Each treatment group was consisted of 8 tumor-bearing mice. Vehicle (DMSO) or ITE in the vehicle at specified doses were administered to the mice by either i.p. (intraperitoneal) or p.o. (oral) injection once or twice daily for 28 continuous days as indicated.

Tumor volume was measured twice weekly in two dimensions using a caliper and the volume was calculated with a formula of: $V=0.5 \, a \times b^2$, where a and b are the long and short diameter (in mm) of a tumor, respectively. The tumor volume was then used for calculations of both TGI (Tumor Growth Inhibition) and TGD (Tumor Growth Delay). The TGI was determined by: $TGI=\Delta T/\Delta C \times 100\%$, where $\Delta T$ was a difference between the mean tumor volume at a specified day of observation and that at the day treatment starts (day 1) for a drug treated group whereas $\Delta C$ was the same difference measured for the control group. The TGD was calculated as: $TGD=T-C$, where T was the time (in days) required for tumors in a drug treated group to reach a predetermined mean tumor volume and C the time (in days) in the control group to reach the same volume. A tumor weight was derived by equating 1,000 mm$^3$ in volume to 1,000 mg in weight. A net body weight was then derived by subtracting a tumor weight from a corresponding gross body weight with the tumor.

Summary statistics, including mean and the standard error of the mean (SEM), are provided for the tumor volume of each group at each time point. Statistical analysis of difference in tumor volume among groups was conducted on a data set either at the best therapeutic time point or at the final dosing day as indicated. The tumor volume data were log-transformed and evaluated using a one-way ANOVA followed by Tukey's test when significance was observed. All data were analyzed using SPSS 16.0 and p<0.05 was considered to be statistically significant.

PK Studies

Male nude mice were also used in PK (pharmacokinetic) studies. For i.v. injection, ITE at 1 mg/kg b.w. was administered with DMSO as vehicle via tail vein. For i.p. Injection, ITE at 10, 40, and 80 mg/kg b.w. was delivered with DMSO via lower left abdominal quadrant. In p.o. injection, ITE at 40 and 80 mg/kg b.w. were administered with a vehicle of Labrasol:PEG 400 (2:8, v/v) via oral gavage. Every 15 mice were given a single injection at each dosing level and every 3 of the dosed mice were used to collect blood sample at each time point (0, 0.083, 0.25, 0.5, 1, 2, 4, 8, 24 hr.). Animals were rotated to be sampled twice each but the duration between the two sampling times was at least 110 min. The animal was anesthetized under Isoflurane and restrained manually. Approximately 150 µl of whole blood at each time point is collected (via retro-orbital puncture) into a $K_2$-EDTA tube. Blood samples were put on ice and processed to plasma (4,000 g, 5 min, 4° C.) within 15 min post sampling. Plasma samples were stored at −80° C. until analysis. An aliquot of 20 µl plasma sample was added with 20 µl of an internal standard (Glipizide, 500 ng/ml in ACN, for extraction efficiency) to 120 µl of ACN (acetonitrile). The mixture was vortexed at 1,500 rpm for 2 min. and then centrifuged at 12,000 rpm for 5 min. Five (5) µl of the supernatant was injected into an LC-MS/MS system (API 4000, Foster City, Calif., USA). A Gemini-C18 column (2.0×50 mm, 5 µm) was used and the LC (liquid chromatography) was run at a flow rate of 0.45 ml/min. with the following program:

| Time (min) | 0.0 | 0.2 | 1.8 | 2.8 | 2.9 | 4.0 |
|---|---|---|---|---|---|---|
| Pump A (%) | 95 | 95 | 2 | 2 | 95 | Stop |
| Pump B (%) | 5.0 | 5.0 | 98 | 98 | 5.0 | Stop | where Pump A was for 1 mM $NH_4OAc$ (ammonium acetate) in water plus 0.025% FA (formic acid) whereas Pump B for 1 mM $NH_4OAC$ in acetonitrile plus 0.025% FA. The negative ionization process of the mass spectrometry was operated at an APCI (Atmospheric Pressure Chemical Ionization) mode while the detection at a MRM (Multiple Reaction Monitoring) mode. ITE was identified by recognizing an LC retention time of 2.5 min. and two mass peaks at 285.0 (before collision) and 142.0 m/z (after collision) while the internal standard of 2.35 min. and two mass peaks at 444.3 (before collision) and 319.3 m/z (after collision). ITE was quantified by a standard curve generated every time by a series of known quantities of ITE running through both the extraction/precipitation process after mixing with mouse plasma and the LC-MS/MS system. The WinNonlin V5.2 statistics software (Pharsight Corporation, California, USA) was used to generate PK parameters such as $C_{max}$, $T_{max}$, $T_{1/2}$, and AUC (Area under Curve) etc. using a non-compartmental model.

Results and Discussion

Treatment with ITE at doses of 1, 10, 20, and 40 mg/kg b.w. (i.p., every 12 hr. for 28 continuous days, DMSO as vehicle, 0.5 ml/kg b.w. as injection volume) produced significant anticancer activities with a clear dose-effect relationship (FIG. 1A). The TGI's (Tumor Growth Inhibition) were calculated as 52%, 31%, 26%, and 22% at day 28 (n=8; p<0.048, 0.007, 0.004, and 0.004), respectively, for the dosing series. The TGD (Tumor Growth Delays) of 3, 10, 12, and 16 days, respectively, at a tumor size of 600 mm$^3$ were attained by the series. ITE at 0.1 mg/kg b.w. didn't produce a statistically significant anticancer activity (n=8, TGI=74% at day 28, p<0.623). Judging from the body weight changes of the tumor-bearing mice, ITE treatment did not seem to provoke significant toxic response (FIG. 1B).

To understand pharmacokinetic (PK) behavior of ITE and direct further efficacy studies, ITE was administered to nude mice in different routes and at different levels. ITE PK profiles are depicted in FIG. 1C. ITE in DMSO at 1 mg/kg b.w. delivered by a bolus i.v. injection was degraded very quickly with an estimated half-life of 6 min. An estimated AUC for the route was 256 hr·ng/ml. ITE in DMSO administered by i.p. injection improved its half-life while the efficiency of absorption was below 10% compared with that of i.v. injection. For example, ITE half-life for 10, 40, and 80 mg/kg b.w. of i.p. injection were 1.13, 1.61, and 5.17 hr., respectively, while AUC for the series was 197, 332, 499 hr·ng/ml, respectively. ITE in Labrasol:PEG 400 (2:8, v/v) delivered via p.o. route had even lower absorption efficiency (around 1%) while kept the half-life to the levels that achieved by i.p. injection. The AUC for the dosing levels of 40 and 80 mg/kg b.w. of p.o. injection was 107 and 97 hr·ng/ml, respectively (FIG. 1C).

Based on the results from PK studies, the schedule, dosing level, and routes of ITE administration were further explored. When a total daily dose was kept the same, the dosing schedule of either once or twice daily for the i.p. route resulted in comparable efficacy in inhibition of cancer growth (e.g. 80 once vs. 40 mg/kg b.w. twice daily, FIG. 1D). Further raising ITE dose to 80 mg/kg (twice daily, i.p.) seemed to further improve the TGI from that of 40 mg/kg (twice daily, i.p.). TGI for 80 mg/kg (twice daily, i.p.) were the best so far obtained, 12% at day 28 and 16% at the last day, for example. Even though absorption efficiency of ITE via p.o. route at a dose of 80 mg/kg was much lower than that of 10 mg/kg i.p. in terms of AUC (FIG. 1C), 80 mg/kg p.o. daily was similar to that of 40 mg/kg i.p. daily in terms of cancer growth inhibition (TGI=46% at day 24, for example) during the first three weeks or so. From the PK studies, ITE plasma level of 80 mg/kg p.o. was lower than that of 10 mg/kg i.p. at the initial hours but became higher than that of 10 mg/kg i.p. and even 40 mg/kg i.p. during hour 3 to 8 post injection (FIG. 1C). That may be the reason behind the results of p.o. injection during the first three weeks. For the p.o. injection, its therapeutic efficacy somehow would not hold longer than that of i.p. injections toward and post the end of treatment (FIG. 1D).

Example 2

Materials and Methods

The culture and inoculation of human prostate cancer cell line LNCaP were as described in Example 1. The manipulation for human liver cancer cell line HepG2 (ATCC) was similar as that for LNCaP except that DMEM (instead of RPMI-1640) medium was used, the L-glutamine was not used, and 2×10$^6$ cells were used for inoculation into female nude mice. The handling of human ovarian cancer cell line OVCAR-3 (ATCC) was the same as that of LNCaP except that the DMEM medium was used and 5×10$^6$ cells were used for inoculation into female nude mice. The human breast cancer cell line MCF-7 (CL-161) is a cloned line from MCF-7 (ATCC) and the growth of its xenografts no longer needs exogenous supply of estrogen. The culture of the MCF-7 cells was similar as that of LNCaP except that MEM medium supplemented with 1 mM non-essential amino acids, 1 mM sodium pyruvate, and 0.01 mg/ml bovine insulin was used to replace RPMI-1640 medium. The inoculation of MCF-7 cells was the same as that of LNCaP except that 0.1 ml of PBS with Matrigel (1:1) and female mice were used for tumor development.

Source of ITE is the same as that described in Example 1. The compound ITK (Structural Formula 2), one of ITE structural analogs, was synthesized by Shanghai ChemPartner Co., Ltd. (Shanghai, China). The lot number was: AhR-ITK-001.

Results and Discussion

ITK (one of ITE structural analogs) was shown to be efficacious at 20 mg/kg b.w. (i.p. once daily) and performed even better than ITE in the same regimen in human prostate cancer (LNCaP) xenograft model (FIG. 2A). The TGI's (Tumor Growth Inhibition) were 51% (p<0.003, n=8) and 64% (p<0.021, n=8) for ITK and ITE, respectively, at day 28. The TGD's (Tumor Growth Delay) for ITK and ITE were 16 and 8 days, respectively, at a tumor volume of 1,000 mm$^3$.

Both ITE and ITK at 80 mg/kg (i.p. once daily) demonstrated good efficacy in inhibiting the growth of human liver cancer (HepG2) xenografts. The performance of ITE and ITK was very comparable in this model (FIG. 2B). The TGI's for ITE and ITK were 25% (p<0.001, n=8) and 22% (p<0.001, n=8), respectively, at day 22. The TGD's were 29 and 26 days at a tumor volume of 800 mm$^3$ for ITE and ITK, respectively. There was no obvious net body weight loss (data not shown) even though there was 1 out of 8 mice in ITK group died at day 32.

Both ITE and ITK at 80 mg/kg (i.p. once daily) again demonstrated a similar efficacy in inhibiting human ovarian cancer (OVCAR-3) growth (FIG. 2C). The TGI's were 47% (p<0.002, n=8) and 46% (p<0.001, n=8) at day 33 for ITE and ITK, respectively. The TGD's for ITE and ITK were, respectively, 10 and 13 days at a tumor volume of 800 mm$^3$. There was no obvious net body weight loss (data not shown). There was again 1 out of 8 mice in ITK group died also at day 32.

ITE displayed a modest efficacy, albeit at a modest dose (20 mg/kg, i.p. once daily), in inhibiting human breast cancer (MCF-7) growth (FIG. 2D). A TGI was calculated as 71% (p<0.031, n=8) at day 19 for the ITE treatment. A TGD of 3 days at a tumor volume of 500 mm$^3$ was obtained for ITE group. Further increase in dosing levels is certainly needed to yield a better growth inhibition and delay but the response of MCF-7 xenografts to ITE treatment was there.

The performance of one of ITE structural analogs (ITK) in this Example validates a huge potential of ITE analog development based on a framework specified by the Structural Formula 4. In addition, an analog with a thiol ester functional group replacing the normal (oxygen) ester in the ITE structure is envisioned to be specially important given the results of ITK (Structural Formula 2) studies. The thiol (S, sulfur) ester so specified by the Structural Formula 3 is thus abbreviated as ITSE. The structural feature of both ITK and ITSE may help fend against attacks by numerous esterases in biological systems specifically to the oxygen ester functional group on the structure of ITE.

Example 3

Materials and Methods

Murine Lewis lung cancer cell line LLC (ATCC) was cultured as described for LNCaP in Example 1 except DMEM, instead of RPMI-1640, medium being used. Each female C57BL/6 mice, 6 to 8 weeks of age, was inoculated with $3 \times 10^5$ LLC cells in 0.1 ml of PBS for tumor development. ITE treatment was started when a mean tumor volume reached 80 to 120 mm$^3$. All the other materials and methodologies were the same as that described in Example 1.

Results and Discussion

The benefit of using xenograft model is that human cancers can be directly tested on animals. The disadvantage, however, is that the mice have to have defects in their immune systems so that they will not reject human cancer cells. It is obvious, therefore, that this type of models cannot be used to test if ITE can stimulate immune system to dramatically enhance its therapy. A syngeneic model, mouse tumor cells inoculated to mice with healthy immune systems, was then used. At a dose of 20 mg/kg b.w. (i.p. once daily), while ITE showed a growth inhibition of the mouse lung cancer (n=8, TGI=65% at day 15, FIG. 3A), there was no indication of cancer elimination or eradication. In fact, the tumor growth was so aggressive in this model that the experiment had to be stopped earlier to relieve the suffering of animals in both control and ITE groups from heavy tumor burdens.

Figure 3D:
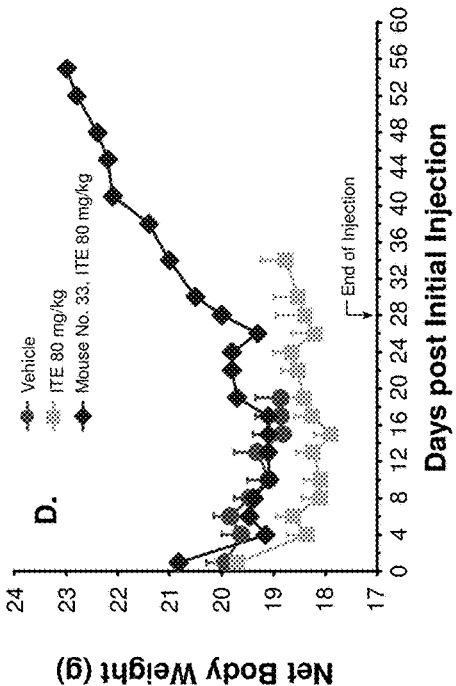
Figure 3A:
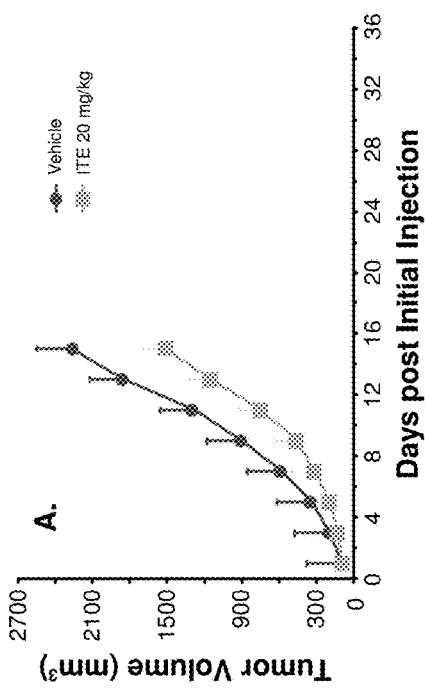
Figure 3C:
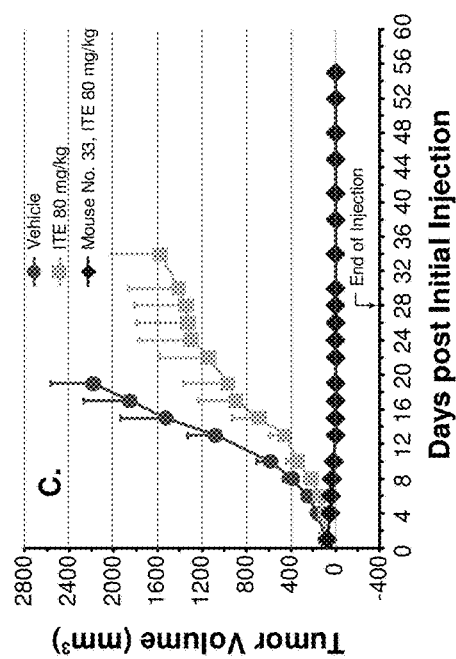

At a dose of 80 mg/kg b.w. (i.p. once daily), ITE significantly improved the growth inhibition of tumors so that ITE treated group could then be kept to the end of the experiment without early termination (FIG. 3B) like before. The TGI at day 20 for ITE treatment was 42% (n=8, p<0.037) and TGD at a tumor volume of 1000 mm$^3$ was 7 days. One of the mice in ITE group (mouse No. 33) started to shrink its tumor upon the start of ITE treatment and kept doing so until its tumor was no longer palpable at day 13 (FIG. 3C). The mouse kept tumor free during the rest of the ITE treatment phase (total 28 days). One more month was then given to the mouse after the stop of the 28-day treatment to show possible regrowth of its tumor. But that did not happen and the mouse kept tumor free during the entire month of observation, suggesting the elimination of every cancer cell by the treatment (FIG. 3C). Body weight change monitoring indicated the mouse No. 33 and the other mice in ITE group tolerated well to the treatment (FIG. 3D).

With xenograft models, complete tumor elimination has never happened at a dose of 80 mg/kg b.w. (i.p. once daily) or even at 80 mg/kg dosed (i.p.) twice a day. That may argue for the stimulation of immune systems in mice of this syngeneic model. Actually, results in Example 4 below may also support this notion by showing increased counts of white blood cells, neutrophils, lymphocytes, and platelets at high (500 mg/kg, i.p. once daily) and mid (100 mg/kg, i.p. once daily) but not low (20 mg/kg, i.p. once daily) dose. Cancer eradication thus may be achieved if immune system could be mobilized to help fighting cancers and cleaning up individual cancer cells while cancer growth could be effectively inhibited and assaulted at the same time.

Example 4

Material and Methods

ITE nano-suspension was prepared by milling ITE powder in water containing 1% CMC-Na (sodium carboxymethyl cellulose), 0.5% SLS (sodium lauryl sulfate), 0.085% PVP K90 (polyvinylpyrrolidone K90), and 0.2% Benzoate with a Media Wet Milling Machine (Dispermat SL-nano, WAB Willy A. Bachofen A G, Muttenz, Switzerland) until reached a desired size range. The particle size was determined by a Laser Diffraction Particle Size Analyzer (MS2000, Malvern Instruments, Worcestershire, UK). The parameters of particle sizes were determined as D10 (diameter of 10% of particles)=67 nm, D50=114 nm, and D90=207 nm. The nano-suspension thus prepared was stored at 4° C. until use.

Female C57BL/6 mice, 6 to 8 week old, were randomly assigned to 4 dose groups (0, 20, 100, and 500 mg/kg b.w.) each with 6 animals. ITE nano-suspension was administered by i.p. injection once daily for 7 consecutive days. Mortality, clinical signs, body weight, and food consumption were recorded. Data on hematology (3 of 6 mice) and serum chemistry (the other 3 of 6 mice) were collected. TK (Toxicokinetic) parameters were determined as described in Example 1 and plasma levels of ITE at both 1 and 3 hr. post dosing on day 1, 3, and 7 were measured. A gross observation of major organs at necropsy was conducted.

Results and Discussion

TK data confirmed the proper ITE system exposure (data not shown). There was no mortality observed except that one mouse in 20 mg/kg b.w. (low dose) group died without known cause before the second day of dosing. There was no significant body weight loss due to ITE treatments even though a dramatic decrease in food consumption in all 3 ITE treated groups was noticed at day 1 of the study. No abnormality was observed from major organ inspection of all the ITE treated groups at necropsy. Levels of ALT (alanine aminotransferase), AST (aspartate aminotransferase), and TP (total protein) of 500 mg/kg (high dose) group was raised by 3.2 (p<0.05), 1.8 (not significant), and 1.2 (p<0.05) folds, respectively, over vehicle control (Table 1). BUN (blood urea nitrogen) of 20 mg/kg (low dose) group was raised by 1.4 folds (p<0.05) over vehicle. These data, especially that of ALT, may suggest an approaching near to the up limit of ITE dosing. WBC (white blood cell count) was raised by 2.6 (p<0.05) and 2.0 folds (not significant) for 100 (mid) and 500 mg/kg (high) group, respectively. Others like percentage of PLT (platelets), percentage of NEUT (neutrophils), numbers of neutrophils (#NEUT), and numbers of lymphocytes (#LYMPH) were increased in both 100 and 500 mg/kg groups albeit not statistically significant (Table 1). Data in hematology, even though more confirmatory studies need to be done, may actually suggest the mobilization of the immune system by ITE, thus reverberating probably to the data of cancer eradication presented in Example 3.

TABLE 1

Partial readings on hematology and serum chemistry

| Dose (mg/kg) | ALT (U/L) | AST (U/L) | BUN (mmol/L) | TP (g/L) | WBC ($\times 10^9$ cells) | PLT ($\times 10^9$ cells) | NEUT (%) | #NEUT ($\times 10^9$ cells) | #LYMPH ($\times 10^9$ cells) |
|---|---|---|---|---|---|---|---|---|---|
| 0 | 23.6 (6.4) | 84.3 (37.9) | 7.6 (1.2) | 39.7 (3.3) | 4.22 (1.85) | 539 (218) | 19.4 (4) | 0.87 (0.67) | 3.09 (1.82) |
| 20 | 43.2 (43.7) | 118.1 (41.7) | 10.5* (0.3) | 39.5 (2.7) | 4.68 (0.04) | 435 (295) | 23.3 (no) | 1.08 (no) | 3.35 (no) |

TABLE 1-continued

Partial readings on hematology and serum chemistry

| Dose (mg/kg) | ALT (U/L) | AST (U/L) | BUN (mmol/L) | TP (g/L) | WBC (×10⁹ cells) | PLT (×10⁹ cells) | NEUT (%) | #NEUT (×10⁹ cells) | #LYMPH (×10⁹ cells) |
|---|---|---|---|---|---|---|---|---|---|
| 100 | 33.2 (10.2) | 131.6 (27.8) | 7.3 (1.6) | 40.8 (3.3) | 10.77* (4.26) | 668 (202) | 46.6 (no) | 3.62 (no) | 3.5 (no) |
| 500 | 74.5* (21.6) | 151.2 (37.1) | 9.1 (0.3) | 49.5* (1.5) | 8.38 (1.32) | 1075 (99) | 40.5 (3.4) | 3.4 (0.64) | 4.81 (0.81) |

Table 1 displays partial readings on hematology and serum chemistry, wherein the listed are group means with SD (standard deviation) inside the parentheses, and wherein the * depicts a statistical significance (p < 0.05), and wherein the "no" means a standar d deviation is not available due to sample size, and wherein ALT means alanine aminotransferase, AST asparta te aminotransferase, TP total protein, BUN blood urea nitrogen, WBC white blood cell count, PLT platelet, NEUT neutrophils, #NEUT number of neutrophils, an d #LYMPH number of lymphocytes.

INDUSTRIAL APPLICABILITY

The present invention can be applied to the area of cancer intervention or eradication for human beings and other animals, especially mammals.

REFERENCE SIGNS LIST

As used herein, the term "structural analog" or simply "analog" of ITE is defined as a compound with chemical structure similar to that of AhR endogenous ligand ITE.

As used herein, the term "alkyl" represents a group of hydrogen saturated one to six carbons connected in either straight or branched fashion.

As used herein, the term "haloalkyl" represents an alkyl substituted by one or more halogen atoms.

As used herein, the term "alkenyl" represents a group of hydrocarbons containing two to six carbons connected in either straight or branched fashion with at least one carbon-to-carbon double bond.

As used herein, the term "alkynyl" represents a group of hydrocarbons containing two to six carbons connected in either straight or branched fashion with at least one carbon-to-carbon triple bond.

As used herein, the term "halo" represents any of halogen atoms (F, Cl, Br, or I).

As used herein, the term "carbonyl" represents:

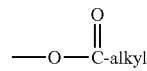

As used herein, the term "alkanoyl" represents an alkyl connected to a carbonyl group:

As used herein, the term "haloalkanoyl" represents a haloalkyl connected to a carbonyl group:

As used herein, the term "nitrogen protective group" represents groups commonly used to protect nitrogen from undesired chemical reactions during synthesis procedures.

As used herein, the term "amino" represents —NR$_a$R$_b$ where R$_a$ and R$_b$ can be independently selected from hydrogen, halo, formyl (—CHO), alkyl, haloalkyl, alkenyl, alkynyl, alkanoyl, haloalkanoyl, or a nitrogen protective group.

As used herein, the term "alkoxy" represents an alkyl connected to an oxygen atom (—O-alkyl).

As used herein, the term "haloalkoxy" represents a haloalkyl connected to an oxygen atom (—O-haloalkyl).

As used herein, the term "thioalkoxy" represents an alkyl connected to a sulfur atom (—S-alkyl).

As used herein, the term "carbonyloxy" represents an alkanoyl connected to an oxygen atom:

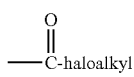

CITATION LIST

Patent Literature

7. DeLuca H F, Clagett-Dame M, Song J, Helfand S, Akhtar N. U.S. Pat. No. 7,419,992—Use of aryl hydrocarbon receptor ligand as a therapeutic intervention in angiogenesis-implicated disorders. 2008.
10. DeLuca H F, Jiasheng Song, Clagett-Dame M, et al. U.S. Pat. No. 6,916,834—Preparations and use of an Ah receptor ligand, 2-(1'H-indole-3'-carbonyl)-thiazole-4-carboxylic acid methyl ester. 2005.

Non Patent Literature

1. Poland A, Knutson J C. 2,3,7,8-tetrachlorodibenzo-p-dioxin and related halogenated aromatic hydrocarbons: examination of the mechanism of toxicity. *Annu. Rev. Pharmacol. Toxicol.* 1982; 22:517-554.
2. Poellinger L. Mechanistic aspects—the dioxin (aryl hydrocarbon) receptor. *Food Addit Contam.* 2000; 17(4): 261-6.
3. Bock K W, Köhle C. Ah receptor- and TCDD-mediated liver tumor promotion: clonal selection and expansion of cells evading growth arrest and apoptosis. *Biochem. Pharmacol.* 2005; 69(10):1403-1408.
4. Stevens E A, Mezrich J D, Bradfield C A. The aryl hydrocarbon receptor: a perspective on potential roles in the immune system. *Immunology.* 2009; 127(3):299-311.
5. Puga A, Tomlinson C R, Xia Y. Ah receptor signals cross-talk with multiple developmental pathways. *Biochem Pharmacol.* 2005; 69(2): 199-207.
6. Safe S, McDougal A. Mechanism of action and development of selective aryl hydrocarbon receptor modulators for treatment of hormone-dependent cancers (Review). *Int J Oncol.* 2002; 20(6):1123-8.

8. Dietrich C, Kaina B. The aryl hydrocarbon receptor (AhR) in the regulation of cell-cell contact and tumor growth. *Carcinogenesis*. 2010; 31(8):1319-1328.
9. Song J, Clagett-Dame M, Peterson R E, et al. A ligand for the aryl hydrocarbon receptor isolated from lung. *Proc Natl Acad Sci USA*. 2002; 99(23):14694-9.
11. Fritz W A, Lin T, Safe S, Moore R W, Peterson R E. The selective aryl hydrocarbon receptor modulator 6-methyl-1,3,8-trichlorodibenzofuran inhibits prostate tumor metastasis in TRAMP mice. *Biochem. Pharmacol.* 2009; 77(7):1151-1160.
12. McDougal A, Wilson C, Safe S. Inhibition of 7,12-dimethylbenz[a]anthracene-induced rat mammary tumor growth by aryl hydrocarbon receptor agonists. *Cancer Lett.* 1997; 120(1):53-63.
13. Holcomb M, Safe S. Inhibition of 7,12-dimethylbenzanthracene-induced rat mammary tumor growth by 2,3,7,8-tetrachlorodibenzo-p-dioxin. *Cancer Lett.* 1994; 82(1): 43-7.
14. McDougal A, Wormke M, Calvin J, Safe S. Tamoxifen-induced antitumorigenic/antiestrogenic action synergized by a selective aryl hydrocarbon receptor modulator. *Cancer Res.* 2001; 61(10):3902-3907.
15. Gierthy J F, Bennett J A, Bradley L M, Cutler D S. Correlation of in vitro and in vivo growth suppression of MCF-7 human breast cancer by 2,3,7,8-tetrachlorodibenzo-p-dioxin. *Cancer Res.* 1993; 53(13):3149-3153.
16. Zhang S, Lei P, Liu X, et al. The aryl hydrocarbon receptor as a target for estrogen receptor-negative breast cancer chemotherapy. *Endocr. Relat. Cancer.* 2009; 16(3): 835-844.
17. Kawajiri K, Kobayashi Y, Ohtake F, et al. Aryl hydrocarbon receptor suppresses intestinal carcinogenesis in ApcMin/+ mice with natural ligands. *Proc. Natl. Acad. Sci. U.S.A.* 2009; 106(32): 13481-13486.
18. Simon T, Aylward L L, Kirman C R, Rowlands J C, Budinsky R A. Estimates of cancer potency of 2,3,7,8-tetrachlorodibenzo(p)dioxin using linear and nonlinear dose-response modeling and toxicokinetics. *Toxicol. Sci.* 2009; 112(2):490-506.
19. Ishida M, Mikami S, Kikuchi E, et al. Activation of the aryl hydrocarbon receptor pathway enhances cancer cell invasion by upregulating the MMP expression and is associated with poor prognosis in upper urinary tract urothelial cancer. *Carcinogenesis*. 2010; 31(2):287-295.
20. Ray S, Swanson H I. Activation of the aryl hydrocarbon receptor by TCDD inhibits senescence: a tumor promoting event? *Biochem. Pharmacol.* 2009; 77(4):681-688.
21. Knerr S, Schrenk D. Carcinogenicity of 2,3,7,8-tetrachlorodibenzo-p-dioxin in experimental models. *Mol Nutr Food Res.* 2006; 50(10):897-907.
22. John A R, Bramhall S R, Eggo M C. Antiangiogenic therapy and surgical practice. *Br J Surg.* 2008; 95(3):281-293.
23. Roukos D H, Tzakos A, Zografos G. Current concerns and challenges regarding tailored anti-angiogenic therapy in cancer. *Expert Rev Anticancer Ther.* 2009; 9(10):1413-1416.
24. English B C, Price D K, Figg W D. VEGF inhibition and metastasis: possible implications for antiangiogenic therapy. *Cancer Biol. Ther.* 2009; 8(13):1214-1225.
25. Loges S, Mazzone M, Hohensinner P, Carmeliet P. Silencing or fueling metastasis with VEGF inhibitors: antiangiogenesis revisited. *Cancer Cell.* 2009; 15(3):167-170.
26. Ebos J M L, Lee C R, Cruz-Munoz W, et al. Accelerated metastasis after short-term treatment with a potent inhibitor of tumor angiogenesis. *Cancer Cell.* 2009; 15(3):232-239.
27. Paez-Ribes M, Allen E, Hudock J, et al. Antiangiogenic therapy elicits malignant progression of tumors to increased local invasion and distant metastasis. *Cancer Cell.* 2009; 15(3):220-231.
28. Quintana F J, Basso A S, Iglesias A H, et al. Control of T(reg) and T(H)17 cell differentiation by the aryl hydrocarbon receptor. *Nature*. 2008; 453(7191):65-71.
29. Henry E C, Bemis J C, Henry O, Kende A S, Gasiewicz T A. A potential endogenous ligand for the aryl hydrocarbon receptor has potent agonist activity in vitro and in vivo. *Arch. Biochem. Biophys.* 2006; 450(1):67-77.
30. Brauze D, Widerak M, Cwykiel J, Szyfter K, Baer-Dubowska W. The effect of aryl hydrocarbon receptor ligands on the expression of AhR, AhRR, ARNT, Hif1alpha, CYP1A1 and NQO1 genes in rat liver. *Toxicol. Lett.* 2006; 167(3):212-220.
31. Bermúdez de Leon M, Gomez P, Elizondo G, et al. Beta-naphthoflavone represses dystrophin Dp71 expression in hepatic cells. *Biochim. Biophys. Acta.* 2006; 1759(3-4):152-158.
32. Okino S T, Pookot D, Basak S, Dahiya R. Toxic and chemopreventive ligands preferentially activate distinct aryl hydrocarbon receptor pathways: implications for cancer prevention. *Cancer Prev Res* (Phila Pa.). 2009; 2(3):251-256.
33. Morrow D, Qin C, Smith R, Safe S. Aryl hydrocarbon receptor-mediated inhibition of LNCaP prostate cancer cell growth and hormone-induced transactivation. *J. Steroid Biochem. Mol. Biol.* 2004; 88(1):27-36.
34. Sanderson J T, Slobbe L, Lansbergen G W, Safe S, van den Berg M. 2,3,7,8-Tetrachlorodibenzo-p-dioxin and diindolylmethanes differentially induce cytochrome P450 1A1, 1B1, and 19 in H295R human adrenocortical carcinoma cells. *Toxicol. Sci.* 2001; 61(1):40-48.
35. Elizondo G, Fernandez-Salguero P, Sheikh M S, et al. Altered cell cycle control at the G(2)/M phases in aryl hydrocarbon receptor-null embryo fibroblast. *Mol Pharmacol.* 2000; 57(5):1056-63.
36. Puga A, Marlowe J, Barnes S, et al. Role of the aryl hydrocarbon receptor in cell cycle regulation. *Toxicology*. 2002; 181-182:171-7.
37. Marlowe J L, Knudsen E S, Schwemberger S, Puga A. The aryl hydrocarbon receptor displaces p300 from E2F-dependent promoters and represses S phase-specific gene expression. *J Biol Chem.* 2004; 279(28):29013-22.
38. Kajta M, Wójtowicz A K, Maćkowiak M, Lasoń W. Aryl hydrocarbon receptor-mediated apoptosis of neuronal cells: a possible interaction with estrogen receptor signaling. *Neuroscience*. 2009; 158(2):811-822.
39. Singh N P, Nagarkatti M, Nagarkatti P. Primary peripheral T cells become susceptible to 2,3,7,8-tetrachlorodibenzo-p-dioxin-mediated apoptosis in vitro upon activation and in the presence of dendritic cells. *Mol. Pharmacol.* 2008; 73(6):1722-1735.
40. Park K, Mitchell K A, Huang G, Elferink C J. The aryl hydrocarbon receptor predisposes hepatocytes to Fas-mediated apoptosis. *Mol Pharmacol.* 2005; 67(3):612-22.
41. Jux B, Kadow S, Esser C. Langerhans cell maturation and contact hypersensitivity are impaired in aryl hydrocarbon receptor-null mice. *J. Immunol.* 2009; 182(11): 6709-6717.
42. Sutter C H, Yin H, Li Y, et al. EGF receptor signaling blocks aryl hydrocarbon receptor-mediated transcription 43. Hall J M, Barhoover M A, Kazmin D, et al. Activation of the Aryl-Hydrocarbon Receptor Inhibits Invasive and Metastatic Features of Human Breast Cancer Cells and Promotes Breast Cancer Cell Differentiation. *Mol Endocrinol.* 2009. Available at: http://www.ncbi.nlm.nih.gov/pubmed/20032195 [Accessed Jan. 27, 2010].

44. Oenga G N, Spink D C, Carpenter D O. TCDD and PCBs inhibit breast cancer cell proliferation in vitro. *Toxicol In Vitro.* 2004; 18(6):811-9.

45. Jana N R, Sarkar S, Ishizuka M, et al. Cross-talk between 2,3,7,8-tetrachlorodibenzo-p-dioxin and testosterone signal transduction pathways in LNCaP prostate cancer cells. *Biochem Biophys Res Commun.* 1999; 256(3):462-8.

46. Morrow D, Qin C, Smith R, Safe S. Aryl hydrocarbon receptor-mediated inhibition of LNCaP prostate cancer cell growth and hormone-induced transactivation. *J Steroid Biochem Mol Biol.* 2004; 88(1):27-36.

47. Veldhoen M, Hirota K, Westendorf A M, et al. The aryl hydrocarbon receptor links TH17-cell-mediated autoimmunity to environmental toxins. *Nature.* 2008; 453(7191):106-109.

48. Koliopanos A, Kleeff J, Xiao Y, et al. Increased arylhydrocarbon receptor expression offers a potential therapeutic target for pancreatic cancer. *Oncogene.* 2002; 21(39):6059-70.

49. Kashani M, Steiner G, Haitel A, et al. Expression of the aryl hydrocarbon receptor (AhR) and the aryl hydrocarbon receptor nuclear translocator (ARNT) in fetal, benign hyperplastic, and malignant prostate. *Prostate.* 1998; 37(2):98-108.

50. Gluschnaider U, Hidas G, Cojocaru G, et al. beta-TrCP inhibition reduces prostate cancer cell growth via upregulation of the aryl hydrocarbon receptor. *PLoS ONE.* 2010; 5(2):e9060.

51. Peng T, Chen J, Mao W, et al. Potential therapeutic significance of increased expression of aryl hydrocarbon receptor in human gastric cancer. *World J. Gastroenterol.* 2009; 15(14):1719-1729.

What is claimed is:

1. A method of stimulating the immune system in a patient in need thereof, comprising administering a therapeutically effective amount of ITE or a structural analog thereof to the patient, wherein ITE has structural formula 1:

Structural Formula 1

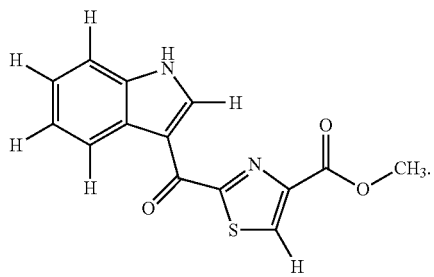

2. The method of claim 1, wherein the ITE structural analog is a compound of structural formula 2:

Structural Formula 2

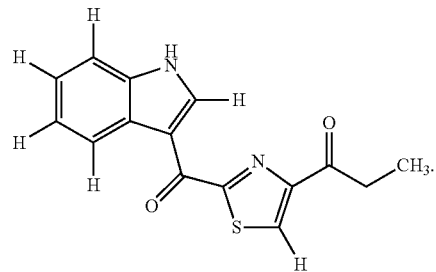

3. The method of claim 1, wherein the ITE structural analog is a compound of structural formula 3:

Structural Formula 3

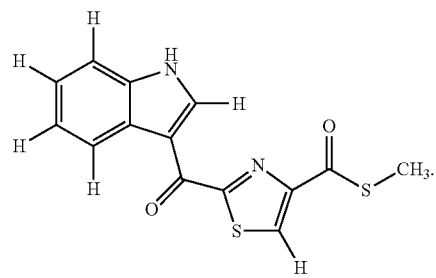

4. The method of claim 1, wherein the ITE structural analog is a compound of structural formula 4:

Structural Formula 4

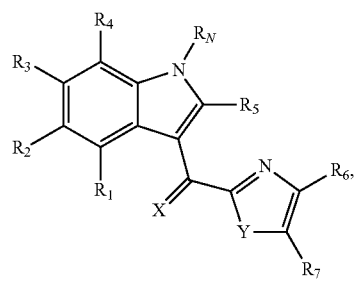

wherein:

X and Y are independently selected from the group consisting of O (oxygen) and S (sulfur);

$R_N$ is selected from the group consisting of hydrogen, halo, cyano, formyl, alkyl, haloalkyl, alkenyl, alkynyl, alkanoyl, haloalkanoyl, and a nitrogen protective group;

$R_1$, $R_2$, $R_3$, $R_4$, and $R_5$ are independently selected from the group consisting of hydrogen, halo, hydroxy, thiol, cyano, formyl, alkyl, haloalkyl, alkenyl, alkynyl, amino, nitro, alkoxy, haloalkoxy, thioalkoxy, alkanoyl, haloalkanoyl, and carbonyloxy;

$R_7$ is selected from the group consisting of hydrogen, halo, hydroxy, thiol, cyano, formyl, alkyl, haloalkyl, alkenyl, alkynyl, amino, nitro, alkoxy, haloalkoxy, and thioalkoxy; and $R_6$ is

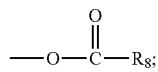

wherein $R_8$ is selected from the group consisting of hydrogen, halo, cyano, alkyl, haloalkyl, alkenyl, and alkynyl; or $R_6$ is

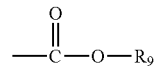

wherein $R_9$ is selected from the group consisting of hydrogen, halo, alkyl, haloalkyl, alkenyl, and alkynyl; or $R_6$ is

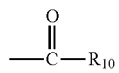

wherein $R_{10}$ is selected from the group consisting of hydrogen, halo, hydroxy, thiol, cyano, alkyl, haloalkyl, alkenyl, alkynyl, and nitro; or $R_6$ is

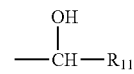

wherein $R_{11}$ is selected from the group consisting of hydrogen, halo, alkyl, haloalkyl, alkenyl, and alkynyl.

5. The method of claim 1, wherein the patient has an increased count of cells selected from the group consisting of white blood cells, neutrophils, lymphocytes, and platelets after the administering step.

6. The method of claim 1, comprising administering a therapeutically effective amount of ITE to the patient.

7. The method of claim 6, wherein the patient has an increased count of white blood cells after the administering step.

8. The method of claim 6, wherein the patient has an increased count of neutrophils after the administering step.

9. The method of claim 6, wherein the patient has an increased count of lymphocytes after the administering step.

10. The method of claim 6, wherein the patient has an increased count of platelets after the administering step.

* * * * *